United States Patent [19]

Nambu

[11] 4,329,529

[45] May 11, 1982

[54] TRACTION FLUIDS FOR TRACTION DRIVE TRANSMISSIONS

[75] Inventor: Masao Nambu, Yokohama, Japan

[73] Assignee: Nippon Oil Co., Ltd., Tokyo, Japan

[21] Appl. No.: 239,800

[22] Filed: Mar. 2, 1981

Related U.S. Application Data

[63] Continuation of Ser. No. 75,301, Sep. 12, 1979, abandoned.

[30] Foreign Application Priority Data

Sep. 19, 1978 [JP] Japan .................................. 53/114103
Sep. 20, 1978 [JP] Japan .................................. 53/114542

[51] Int. Cl.$^3$ ............................................. C07C 13/00
[52] U.S. Cl. ........................................ 585/20; 252/73; 585/25; 585/254; 585/268
[58] Field of Search ...................... 252/73; 585/20, 25, 585/254, 268

[56] References Cited

U.S. PATENT DOCUMENTS

| | | | |
|---|---|---|---|
| 2,386,507 | 10/1945 | Quin | 585/25 |
| 3,272,879 | 9/1966 | Stahly | 585/25 |
| 3,925,217 | 12/1975 | Green et al. | 585/25 |
| 3,975,278 | 8/1976 | Wyqant | 585/25 |

OTHER PUBLICATIONS

Terent'eva et al., Chem. Abs., 63, 6925(b).
Gerber et al., Chem. Abs., 64, 4825h.
Sanin et al., Chem. Abs., 60, 2345h.
Terent'eva et al., Chem. Abs., 57, 9698b.

*Primary Examiner*—Curtis R. Davis
*Attorney, Agent, or Firm*—Jordan and Hamburg

[57] ABSTRACT

Traction fluids for traction drive transmissions, prepared by hydrogenating an alkylation product obtained by the reaction of xylene and/or toluene, together with or without ethylbenzene, with styrene.

22 Claims, No Drawings

TRACTION FLUIDS FOR TRACTION DRIVE TRANSMISSIONS

This is a continuation of application Ser. No. 75,301, filed Sept. 12, 1979, and now abandoned.

This invention relates to fluids, preferably high viscosity fluids, for traction drive transmissions. More particularly, it relates to such fluids obtained by hydrogenating an alkylation product obtained by the reaction of xylene and/or toluene, together with or without ethylbenzene, with styrene.

In the traction drive transmissions, it is required that the traction fluid lose its fluidity by entering a rolling contact point to form a film thereof, at which contact point two cylinders or cones rolling in the directions opposite to each other about their respective fixed rotation axes contact with each other at the surface, and that the traction fluid recover its original fluidity by leaving the contact point. In other words, it is of course desired that the traction fluid will exhibit high rolling friction when used since power is transmitted by means of rolling friction caused by hardening of the film of the traction fluid (the traction fluid in filmy state at high pressures) at the rolling contact point in the traction drive transmissions. The rolling friction property required in a traction fluid is expressed by a rolling friction coefficient measured in the predetermined traction drive transmissions.

There have already been proposed various hydrocarbons and oxgen-containing hydrocarbons as traction fluids as well as the processes for the production thereof. However, there are not known yet traction fluids which may be easily synthesized from industrially easily available inexpensive starting material and will exhibit excellent performance. Conventional traction fluids include decalin, perhydroanthracene (U.S. Pat. No. 3,411,369), polycyclohexyl (ASLE Transactions 13 105 (1970), U.S. Pat. No. 3,925,217), bicyclohexyl and dicyclohexylmethane (U.S. Pat. No. 3,440,894), 2,3-dicyclohexylbutane (Japanese Pat. Appln. Laying-Open Gazette No. 4510/71, hydrogenated oligomers of isobutylene (Japanese Pat. Appln. Laying-Open Gazette Nos. 4766/71, 2164/72 and 2229/72), hydrogenated $\alpha$-methylstyrene cyclized dimer (Japanese Pat. Appln. Laying-Open Gazette No. 2229/72 and Pat. Gazette No. 35763/72) and adamantane (Japanese Patent Gazettes Nos. 42067/73, 42068/73 and 35763/72). However, these conventional traction fluids are unsatisfactory in practical performances, particularly rolling friction coefficient, that is, traction coefficient.

Various studies were made in attempts to eliminate these disadvantages and, as a result, there was proposed a hydrogenated linear dimer of $\alpha$-methylstyrene, that is, 2,4-dicyclohexyl-2-methylpentane (Japanese Pat. Appln. Laying-Open Gazette No. 7664/72, U.S. Pat. Nos. 3,975,278 and 3,994,816) as a synthesized traction fluid having excellent rolling friction coefficient as compared with the aforesaid various conventional hydrocarbons. However, although it is known that the traction fluid so proposed may be industrially synthesized by linearly dimerizing $\alpha$-methylstyrene followed by being hydrogenated, it is disadvantageous that $\alpha$-methylstyrene as the starting material for traction fluids is expensive and the dimerization thereof will be accompanied with side reactions. It is well known that the side reactions in this case include the polymerization (such as trimerization and tetramerization) and cyclization of $\alpha$-methylstyrene. To solve the problem as to these side reactions, there have been proposed methods such as a method comprising pyrolyzing (depolymerizing) polymers (from trimer to heptomer) produced by the side reactions to obtain dimer therefrom (Japanese Pat. Gazette No. 35763/72), a method comprising using both montmorillonite type clay and an organic oxygen compound (Japanese Pat. Appln. Laying-Open Gazette No. 148053/77) and a method comprising using previously heat treated montmorillonite type clay as the catalyst to prevent the cyclization (Japanese Pat. Appln. Laying-Open Gazette No. 21149/78); however, the methods so proposed are not entirely satisfactory in preventing the side reactions. Even if these methods be further improved in side reaction prevention efficiency in the future, they will still have to procure $\alpha$-methylstyrene for use as the starting material, this being economically burdensome. It s considered as the most possible reason why the popularization of traction drive power transmissions is retarded that traction fluids (lubricants for traction drive transmissions) now marketed are expensive, and this would now be tolerated as inevitable since such expensive $\alpha$-methylstyrene has to be used as the starting material although there are difficulties in carrying out the desired dimerization as previously mentioned. It was attempted as the matter of course to use, as the starting material, styrene which was far inexpensive as compared with $\alpha$-methylstyrene; however, it was found that the product thus obtained had a traction coefficient which was about 30% lower than that of products obtained from $\alpha$-methylstyrene as the starting material (Japanese Pat. Gazette No. 35763/72).

In addition, there were also studied the hydrogenation of alkylnaphthalenes, the hydrogenation of naphthenic mineral oils, the hydrogenation of polycondensates of alkylbenzenes with formaldehyde, and the hydrogenation of indane dimer (Japanese Pat. Gazette No. 35763/72). However, the products so obtained were inferior in properties to 2,4-dicyclohexyl-2-methylpentane obtained by dimerizing $\alpha$-methylstyrene and then hydrogenating the thus obtained dimer.

The present inventor made various studies in attempts to produce excellent traction fluids from materials other than $\alpha$-methylstyrene which is expensive, and, as a result of his studies, he found that excellent traction fluids may be obtained by a process comprising alkylating (A) xylene and/or toluene, together with or without ethylbenzene in an amount by weight of less than 50% of the xylene and/or toluene used, with (B) styrene to obtain an alkylation product and then hydrogenating the thus obtained alkylation product.

Xylene or toluene and styrene are comparatively inexpensive starting materials which are industrially readily available as is generally known. However, none of the aforesaid patents and publications disclose that such inexpensive starting materials may be used in obtaining therefrom excellent traction fluids nor do they even suggest that the products so obtained can be unique ones having an excellent traction coefficient.

In a broad sense, this invention is characterized in that xylene and/or toluene, together with or without ethylbenzene, is alkylated with styrene and then hydrogenated. As the starting material, xylene is preferred from the viewpoint of the traction coefficient of final products derived therefrom and readily available mixed xylenes are industrially the most preferred. The "mixed xylene" used herein is a mixture containing, by weight, 10–40% of o-xylene, 20–45% of m-xylene, 10–25% of p-xylene and 0–45% of ethylbenzene, and the presence of less than 50% by weight of ethylbenzene in the mixed xylene will not have any adverse effects on the merits of this invention.

As the starting material, ethylbenzene may be substituted for xylene and toluene, however, it is not particularly advantageous over xylene and/or toluene which is industrially readily available and comparatively inexpensive. Xylene and toluene used are not required to be highly pure and may, without any troubles, coexist with saturated aliphatic or aromatic hydrocarbons having not more than 12 carbon atoms as impurities, the hydrocarbons being typified by hexane, decane and the like. Styrene as the alkylating agent is neither required to be of high purity and may also, without any troubles, be coexistent with aromatic and saturated aliphatic hydrocarbons having not more than 12 carbon atoms such as ethylbenzene, xylene, toluene, decane and dodecane. Further, vinyltoluene, α-methylstyrene, p-methylstyrene and the like may also be used as the alkylating agent, but they are not particularly advantageous over styrene which is comparatively inexpensive.

Conventional known techniques may be applied to a process for the alkylation of xylene and/or toluene with styrene, and, in this case, it is particularly preferable that the ratio of polymerization of the styrene be limited to within 18%. The alkylation process which may be used in this invention is illustrated as follows.

In a case where sulphuric acid is used as the catalyst, xylene (or toluene) cooled to not higher than 30° C., preferably 5°–20° C., was incorporated with sulphuric acid (conc. 75–90 wt.%) in an amount equal to, or less than, that of the xylene (or toluene), agitated, incorporated in small portions (for example, over a time period of 10 minutes to one hour) with styrene in an amount of not more than a half of the xylene (or toluene) while cooling the whole to not higher than 30° C., thereafter agitated for additional 30 minutes to 2 hours for example, incorporated with an aqueous solution of sodium hydroxide to neutralize the reaction system and subjecting the resulting reaction mixture to water washing and fractionation thereby to obtain an alkylation product of xylene (or toluene) in a yield of 82–87%, based on the weight of styrene used. Conventional processes for the alkylation of xylene (or toluene) with styrene in the presence of conc. sulphuric acid as the catalyst may also be used for the purpose of this invention, and, in this case, care should be taken to inhibit side reactions from taking place by controlling particularly the reaction temperature, the rate of addition of the styrene and the agitation of the reaction system thereby to ensure an effective utilization of styrene of, preferably, at least 82% (a ratio of polymerization of styrene being not more than 18%). Solid acids such as silica alumina, which are generally known, may also be used as a catalyst for alkylating aromatic compounds. Also in this case, it is preferable that the ratio of polymerization of styrene be limited to not more than 18% by controlling the reaction conditions and, to this end, it is desirable that, for example, a mixture of xylene (or toluene) and styrene in the ratios of 5–20:1 is passed continuously through a synthetic silica alumina catalyst having a 20–50 wt.% aluminum content obtained by calcining at 450°–600° C., at a reaction temperature of 140°–160° C. and a reaction pressure of 3–10 Kg/cm² under the condition of SV being 0.3–3.0.

The use of sulphuric acid or solid acid as the catalyst and the control of the reaction conditions in the aforesaid manner will result in limiting the styrene polymerization ratio to 7–18%. It is preferable that the styrene polymers produced in this case be separated from the alkylation reaction product in the fractionation step subsequent to the alkylation step.

If the said consideration for the alkylation reaction conditions be neglected, high styrene polymers (tar) as the by-product will remarkably increase in amount and at the same time linear and cyclized styrene dimers will come to be found in the resulting alkylation product, this being advantageous from the view-point of the purity and grade of the alkylation product as well as of the effective use of styrene.

To produce materials corresponding to the alkylation product obtained by the alkylation of xylene (or toluene) with styrene, there have heretofore been tried various methods such as a method comprising treating toluene and methylphenylcarbinol in the presence of aluminum chloride as the catalyst, a method comprising decomposing 2-phenyl-1,2-di-p-tolylpropanone-1, a method comprising treating α-bromoethylbenzene and toluene with zinc powder, a method comprising reducing β,β-dichloro-α-phenyl-α-p-tolylethane with metal sodium, a method comprising treating toluene (or xylene) and vinyl chloride with aluminum chloride and a method comprising alkylating toluene (or xylene) with styrene in the presence of aluminum chloride as catalyst. However, it is preferable from the view-point of the effective use of inexpensive starting materials and the avoidance of dimerization of styrene that xylene (or toluene) is alkylated with styrene under such reaction conditions that sulphuric acid or a solid acid is used as the catalyst and the ratio of polymerization of styrene is limited to not more than 18%.

In one aspect of this invention, firstly at least one member selected from the group consisting of toluene, xylene, and mixtures of at least one of toluene and xylene with ethylbenzene, is reacted with styrene to obtain an alkylation reaction product boiling in the range of preferably 270°–340° C., more preferably 280°–320° C. and secondly the alkylation product so obtained is then hydrogenated to obtain a traction fluid boiling in the range of preferably 270°–300° C. In this case, if the alkylation product is of toluene and styrene origin, it contains as the main component α-phenyl-α-tolylethane (α-methylbenzyltoluene) which boils in the range of 291°–293° C. at atmospheric pressure, in the range of 143°–144° C. (11 mm Hg) or in the range of 154°–155.8° C. (14 mm Hg), has a specific gravity (17/4° C.) of 0.9847 and a refractive index ($n_D^{17}$) of 1.566, while the alkylation reaction product of xylene and styrene origin contains, as the main component, α-phenyl-α-(dimethylphenyl) ethane (α-methylbenzylxylene) which boils in the range of 311°–317° C. at atmospheric pressure or in the range of 240°–243° C. (110 mm Hg) and have a specific gravity (15/4° C.) of 0.987. The thus obtained hydrogenated, alkylation products (hereinafter sometimes referred to as "traction fluids (I)" of toluene according to one aspect of this invention contain, as the main component, α-cyclohexyl-α-methylcyclohexylethane boiling in the range of 271°–273° C. at atmospheric pressure, 151° C. at 24 mm Hg or 140° C. at 14 mm Hg and having a specific gravity (15/4° C.) of 0.88, a refractive index ($n_D^{20}$) of 1.480, a pour point of not higher than −50° C. and a viscosity of 0.5 poise at 0° C. or 2.0 poise at −25° C. In addition, the hydrogenated, alkylation reaction products of xylene contain, as the main component, α-cyclohexyl-α-dimethylcyclohexylethane boiling in the range of 290°–295° C. and having a specific gravity (15/4° C.) of 0.89, a refractive index ($n_D^{20}$) of 1.484, a pour point of −49° C. and a viscosity of 0.5 poise at 0° C. or 3.0 poise at −25° C. In addition, the final products of this invention has a kinetic viscosity of 2–2.2 cSt at 98.9° C.

The hydrogenation may be effected by contacting a mixture of the alkylation reaction product and hydrogen with a catalyst for hydrogenation of aromatic nuclei at not higher than 250° C., the catalyst being typified by nickel, nickel oxide, nickel-atomaceous earth. Raney nickel, nickel-copper, platinum, platinum oxide, platinum-activated carbon, platinum-rhodium, platinum-alumina, platinum-lithium-alumina, rhodium-activated carbon, palladium, cobalt, Raney-cobalt, ruthenium and tungsten sulphide-nickel sulphide-alumina. The hydrogenation may be effected batchwise or continuously, and, at any rate, the alkylation reaction products-hydrogen contact time is desirably such that the aromatic nuclei are almost hydrogenated. If the contact time is shorter than is required and the unreacted aromatic compounds therefore remain, then the resulting traction fluid will have a remarkably decreased traction coefficient. From this view-point, the contact time is preferably such that the aromatics remaining ratio, [(phenyl groups left after hydrogenation mol/l)/(alkylation reaction products mol/l)×2]×100%, is not more than 2% and, particularly preferably, not more than 0.5%. In the hydrogenation of organic compounds, it is customary to shorten the time necessary for contact between the organic compound and hydrogen by raising the hydrogen pressure (reaction pressure) and/or reaction temperature. Such a customary technique is of course effective in the hydrogenation in this invention, however, the use of an unduly high reaction temperature in attempts to achieve perfect hydrogenation will cause dealkylation (or decomposition) of the alkylation reaction product and production of tar therefrom thereby resulting in both a decrease in yield of traction fluids and early degradation of the catalyst for hydrogenation. It is therefore preferable that the temperature for hydrogenating the alkylation reaction product be not higher than 250° C. as previously mentioned. The hydrogenation according to this invention may be effected for a contact time of 30 minutes to 15 hours in the presence of, for example, Raney nickel catalyst at 130°–240° C. and 30–200 atm., Raney cobalt catalyst at 130°–180° C. and 20–200 atm., nickel oxide catalyst at 150°–250° C. and 20–100 atm., nickel-diatomaceous earth catalyst at 120°–200° C. and 10–180 atm.), platinum black catalyst at 100°–250° C. and 80–100 atm., platinum-activated carbon catalyst at 150°–180° C. and 20–80 atm., platinum-alumina catalyst at 200°–250° C. and 27–100 atm. or rhodium-activated carbon at 80°–200° C. and 30 atm. In a case where the alkylation reaction product is contacted with hydrogen for a comparatively long time at a specific reaction temperature of not higher than 180° C., the hydrogenation will proceed substantially without being accompanied with the decomposition and polymerization of the alkylation product whereby the resulting hydrogenated product (that is the alkylation reaction product so hydrogenated) may be used as the traction fluid without any further treatment. However, it is desired from the economical point of view that the contact time be shortened to about 30 minutes-one hour by suitably raising the reaction temperature. In a case where the hydrogenation is made to proceed promptly at such a raised reaction temperature, it will be accompanied with slight decomposition and polymerization of the alkylation product; it is thus preferable that a fractionation step be provided downstream of the hydrogenation step to remove from the reaction mixture xylene (or toluene) as the decomposition product and tar as the polymerizate thereby to obtain a fraction boiling in the range of 270°–300° C. for use as the traction fluid. In this case, so long as the aforesaid considerations for the hydrogenation are taken into account and the hydrogenation is carried out at not higher than 250° C., the loss of the alkylation product caused by the decomposition and polymerization thereof will be limited to 3–4%, based on the weight of the alkylation reaction product used, and, therefore, the yield of a lubricating oil (traction fluid) obtained by the separation of the by-products produced by said decomposition and polymerization will decrease by 4% or less.

With respect to the traction coefficient (rolling friction coefficient) of the xylene and/or toluene alkylation reaction product and those in hydrogenated form according to this invention, the former (non-hydrogenated) exhibit very unsatisfactory results while the latter (hydrogenated) exhibit satisfactory results.

A method for measuring traction coefficients and an apparatus therefor are described in "Junkatsu (Lubrication)" vol. 16, No. 8, p. 573 (1971) and the measurement for traction coefficients in this invention was made in accordance with said known method. More particularly, using a four-roller type friction tester comprising a center roller (dia. 4 cm) being centerlessly supported and three outer rollers (dia. 4 cm each) positioned respectively positioned in contact with the center roller, the three outer rollers being capable of rotating the center roller in the direction opposite to that in which the outer rollers rotate when the outer rollers are each made to rotate at the peripheral velocity (1,500 r.p.m.) in the same direction, a load of 207 Kg is applied to the contact surfaces or points and simultaneously a certain braking torque is applied to the driven rotation axle to differentiate the center roller from the outer rollers in number of rotations (to cause a difference in number of rotations, that is a slippage) thereby directly measuring the torsional moment of the driven axle of the inner cylinder by the use of a resistant wire distortion tester provided on the axle. The test pieces (inner and outer rollers) are made of carbon steel (JIS S45C), "JIS" standing for "Japanese Industrial Standard", and the greatest Hertz load, based on the load applied to the outer rollers, is 93 Kg/mm$^2$. In the measurement of traction coefficients, the temperature of the traction fluid supplied to the test pieces was adjusted to 25° C. unless otherwise specified.

The traction coefficients measured under the aforesaid conditions were 0.047–0.051 for the toluene or xylene alkylation reaction product and 0.088–0.092 for the hydrogenated, toluene or xylene alkylation product of this invention, while the traction coefficients of various hydrocarbons synthesized for comparison were illustrated by 0.062 for a hydrogenated styrene dimer, 0.060 for dicyclohexyl, 0.062 for dicyclohexylmethane, 0.063 for α,β-dicyclohexylmethane, 0.085 for a hydrogenated α-methylstyrene linear dimer, 0.056 for a hydrogenated polyisobutylene, 0.066 for a hydrogenated alkylation product of toluene and formaldehyde, 0.063 for cyclopentyldecalin, 0.061 for cyclopentyldicyclohexyl and 0.065 for dicyclohexylmethylcyclohexane. From the foregoing it is apparent that the hydrogenated, toluene or xylene alkylation products of this invention are remarkably superior in traction coefficient to the ordinary hydrocarbons, and that they are also superior in traction coefficient to hydrogenated α-methylstyrene linear dimers which have heretofore been well known to be hydrocarbons having a high traction coefficient.

In evaluating the performances of traction fluids, the traction coefficient thereof is particularly made much of, however, there are of course further taken into account the oxidation stability, pour point, heat stability, viscosity, viscosity index, flash point, anticorrosiveness against metals, shearing stability, wear resistance and like properties of the traction fluids as is the case with ordinary lubricants. The traction fluids of this invention have satisfactory such performances and properties and, further, they may be incorporated with known additives for traction fluids, such as tricresyl phosphate, 2,6-di-tertiary butyl-p-cresol, polyalkylmethacrylate, alkylene glycol pentaborate, thiophosphate and/or phosphoric acid diesters, as required to improve them in oxidation stability, heat stability, anticorrosiveness against metals, wear resistance, viscosity, viscosity index and the like.

The traction fluids obtained in one aspect of this invention are excellent ones, however, there are not a few cases where traction fluids having further high viscosity (hereinafter sometimes referred to as "traction fluids (II)") are preferred. More particularly, the traction fluids (I) having a kinetic viscosity of 2–2.2 cSt (98.9° C.) are suitable for use as traction fluids in tractors in frigid zone, submarines, vessels sailing in the North and South seas, and the like, while the traction fluids (II) having a kinetic viscosity of 3–11 cSt (98.9° C.) are preferred or required for use as variable ratio transmission oils or bearing oils for variable speed traction drive automobiles, gas turbine engines, grinders, sound apparatuses and the like. In the latter case, the traction fluids (I) and hydrogenated α-methylstyrene dimer are disadvantageous in that they have a relatively low viscosity.

The traction fluids (I) having a kinetic viscosity of 2–2.2 cSt (98.9° C.) and a flash point of 137°–140° C. as well as hydrogenated α-methylstyrene dimer having a kinetic viscosity of 3.7 cSt (98.9° C. ) and a flash point of 149° C. may be used in many of traction drive submissions, however, they are unsatisfactory for use in such traction drive transmissions that are operated under particularly severe conditions (under a heavy load, for example). It is desired that traction fluids suitable for use in such severely operated traction drive transmissions have a kinetic viscosity of 4–11 cSt (98.9° C.) and a flash point as high as possible. As traction fluids having such a high viscosity, there have already been proposed 1-cyclohexyl-1,3,3-trimethylhydrindane (hydrogenated α-methylstyrene cyclic dimer having a kinetic viscosity of 4.16 cSt (98.9° C.)), hydrogenated tricyclopentadiene having a kinetic viscosity of 4.293 cSt (98.9° C.), bisdecalin having a kinetic viscosity of 11.0 cSt (98.9° C.), 1,2,3-tricyclohexylpropane having a kinetic viscosity of 7.687 cSt (98.9° C.) and the like as is shown in U.S. Pat. Nos. 3,411,369 (1968) and 3,440,894 (1969). Among the aforesaid high viscosity traction fluids, 1-cyclohexyl-1,3,3-trimethylhydrindane and hydrogenated tricyclopentadiene are not so different in viscosity from the aforesaid hydrogenated styrene dimer having a kinetic viscosity of 3.7 cSt (98.9° C.), while bisdecalin and 1,2,3-tricyclohexylpropane are noteworthy as a traction fluid of relatively high viscosity. However, bisdecalin is not satisfactory as a traction fluid since it is inferior in traction coefficient to hydrogenated fluorene, hydrogenated phenanthrene and the like as is known from U.S. Pat. No. 3,411,369. 1,2,3-tricyclohexylpropane is neither satisfactory as a traction fluid since it is somewhat excellent in traction coefficient, however, it is still approximately equal to dicyclohexyl in this regard (U.S. Pat. No. 3,440,894). Further, 1,2,3-tricyclohexylpropane is difficult to procure industrially and is not easily available since it is required to be synthesized by hydrogenating a Grignard's reaction product of, for example, phenyl magnesium bromide and 1,3-diphenylacetone. Hydrogenated α-methylstyrene trimer has also been proposed but it is not satisfactory since α-methylstyrene tetra- to hexamers are produced as by-products in the step of polymerization of α-methylstyrene and α-methylstyrene itself is relatively expensive. As an expedient for enhancing viscosity, there has been proposed the addition to a low viscosity traction fluid of hydrogenated polyisobutylene, hydrogenated poly(4-methylpentene-1), hydrogenated poly(2,3-dimethylbutene-1), hydrogenated poly(3-methylbutene-1), a hydrogenated butylmethacrylatelaurylmethacrylate copolymer or the like. However, these additives are not desirable as a component for traction fluids and such an addition method cannot be said to be a satisfactory one from the view-point of traction coefficient, shearing stability, heat stability and like properties of the resulting product even if the additives are effective in enhancing viscosity.

In another aspect of this invention, bis-(α-methylbenzyl) toluene and/or bis-(α-methylbenzyl) xylene may be hydrogenated, or a mixture of at least one of these compounds with bis-(α-methylbenzyl) ethylbenzene may also be hydrogenated, to obtain a traction fluid (traction fluid (II) of this invention) having a higher traction coefficient than the traction fluid (I); in addition, 1-(methylphenyl)-1,3-diphenyl butane and/or 1-(dimethylphenyl)-1,3-diphenyl butane may be hydrogenated, or a mixture of at least one of these compounds with 1-(ethylphenyl)-1,3-diphenyl butane may also be hydrogenated, to obtain a traction fluid (II) having a higher traction coefficient than the traction fluid (I). These compounds to be hydrogenated may conveniently be obtained by alkylating with styrene at least one member selected from the group consisting of toluene, xylene, and mixtures of at least one of them with ethylbenzene.

The traction fluids (II) of this invention may be a compound or a mixture of compounds represented by the following formula

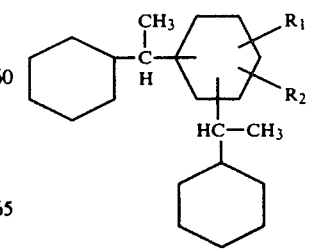

or

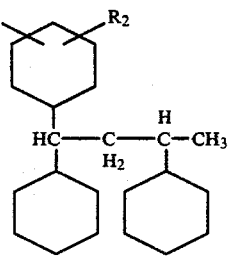

wherein $R_1$ is H or $CH_3$, $R_2$ is $CH_3$ or $C_2H_5$, but $R_2$ does not take $C_2H_5$ when $R_1$ takes $CH_3$. They have a high viscosity of 9.8–10.9 cSt (98.9° C.) and a flash point of 200°–205° C. They therefore meet the requirements of traction fluids (II) contemplated by this invention. In addition, from the result of test for their traction coefficient they have been found to have excellent performances as traction fluids (II).

As mentioned before, it is desirable that the aforesaid bis-(α-methylbenzyl) xylene and the like to be hydrogenated in this invention be obtained by alkylating with styrene a mixture of (1) at least one of xylene and toluene with (2) ethylbenzene in an amount by weight of less than 5% of the xylene and/or toluene used or preferably by alkylating at least one of xylene and toluene with styrene.

It is neither known nor even suggested from any prior art literature that toluene or xylene and styrene, which are easily available for industrial purposes and relatively inexpensive, may be used in producing therefrom high viscosity traction fluids as compared with the traction fluids (I), and that bis-(α-methylbenzyl) toluene, bis-(α-methylbenzyl) xylene, bis-(α-methylbenzyl) ethylbenzene, 1-(methylphenyl)-1,3-diphenylbutane, 1-(dimethylphenyl)-1,3-diphenylbutane, 1-(ethylphenyl)-1,3-diphenylbutane or mixtures thereof, each in hydrogenated form, may be used as particularly excellent traction fluids for traction drive transmissions. In the other aspect of this invention, it is preferable that toluene and/or xylene as well as mixtures thereof with ethylbenzene be alkylated with styrene in the production of bis-(α-methylbenzyl) toluene, bis-(α-methylbenzyl) xylene, bis-(α-methylbenzyl) ethylbenzene, 1-(methylphenyl)-1,3-diphenylbutane, 1-(dimethylphenyl)-1,3-diphenylbutane, 1-(ethylphenyl)-1,3-diphenylbutane or mixtures thereof, and it is characteristic that the alkylation products so obtained are then hydrogenated. In this case, xylene among toluene and xylene is preferred in the respect of traction coefficients of the final products, and mixed xylene easily available for industrial needs is the most preferable as the starting material as previously mentioned. The composition and the like of the mixed xylene are also as previously mentioned.

Bis-(α-methylbenzyl) toluene and bis-(α-methylbenzyl) xylene as well as bis-(α-methylbenzyl) ethylbenzene, 1-(methylbenzyl)-1,3-diphenylbutane, 1-(dimethylphenyl)-1,3-diphenylbutane and 1-(ethylphenyl)-1,3-diphenylbutane, may be produced by using heretofore known catalysts and reaction conditions. It is desirable in this case that, regardless of the kind of the catalyst used, care be taken of the reaction temperature, velocity of addition of styrene and agitation of the reaction system to inhibit the polymerization of styrene as far as possible thereby ensuring an effective styrene utilization ratio of at least 82% (that is, a styrene polymerization ratio of not higher than 18%) as previously mentioned with respect to the traction fluids (I).

Processes for alkylation are described in, for example, Japanese Pat. Appln. Laying-Open Gazettes Nos. 97096/73 and 97858/73. The preferred process is illustrated as follows. In a case where sulphuric acid is used as the catalyst, toluene (or xylene) cooled to 5°–20° C. is incorporated with sulphuric acid (conc. 90–96 wt.%) in an amount by volume less than the toluene (or xylene), agitated, incorporated in small portions with styrene in an amount less than one-fourth of the amount of the toluene (or xylene) over a time period of, for example, 10 minutes to 1 hour while cooling the whole to 5°–20° C., thereafter agitated for 30–60 minutes, neutralized with an aqueous solution of sodium hydroxide, washed with water and then fractionated thereby to obtain bis-(α-methylbenzyl) toluene (or bis-(α-methylbenzyl) xylene) in a yield of about 30%, based on the styrene used. In this case, the greater part of the remaining styrene is consumed in producing therefrom α-methylbenzyltoluene (α-phenyl-α-tolylethane) or α-methylbenzylxylene (α-phenyl-α-(dimethylphenyl) ethane), which is an intermediate of bis-(α-methylbenzyl) toluene or bis-(α-methylbenzyl) xylene. Said intermediate may be incorporated with styrene and sulphuric acid for repeating such an alkylation as above thereby to obtain bis-(α-methylbenzyl) toluene or bis-(α-methylbenzyl) xylene; thus, the total yield of these compounds amounting to at least 80%. In addition, when said starting material is coexistant with ethylbenzene, bis-(α-methylbenzyl) ethylbenzene will be additionally produced.

Solid acids, such as silica alumina, which are known as a catalyst for alkylating aromatic compounds, may be used in this invention as previously mentioned. Regarding the use of the solid acids as a catalyst, considerations of selection of the reaction conditions are described in, for example, British Pat. No. 896864 (1961). In a case where the acid catalyst is used, the optimum reaction conditions to minimize the polymerization of styrene cannot simply be determined since the performance of the catalyst varies depending on the manner in which it is prepared and pretreated. As mentioned before, however, the reaction may be effected by, for example, a mixture of toluene (or xylene) and styrene in a ratio by weight of from 5–20 to 1 may be continuously supplied onto a silica alumina catalyst with a 20–50 wt.% alumina content previously calcined at 450°–600° C., at a temperature of 140°–160° C., a space velocity of 0.3–3.0 (1/hr) and a pressure of 3–10 Kg/cm² thereby to limit the ratio of polymerization of the styrene to 7–15% and convert 85–93% of the styrene to a mixture of α-methylbenzyl toluene (or α-methylbenzyl xylene), bis-(α-methylbenzyl) toluene (or bis-(α-methylbenzyl) xylene) and 1-(methylphenyl)-1,3-diphenylbutane (or 1-(dimethylphenyl)-1,3-diphenylbutane).

The alkylation products of toluene origin which are bis-(α-methylbenzyl) toluene and 1-(methylphenyl)-1,3-diphenylbutane, obtained in the other aspect of this invention are those recovered at a distillation temperature of 348°–362° C. and have a boiling point of 180°–200° C. at 3 mm Hg, a refractive index ($n_D^{20}$) of 1.5663–1.5665, a specific gravity (15°/4° C.) of 0.984–0.985 and a bromine number of not more than 0.05. The alkylation products of xylene origin which are bis-(α-methylbenzyl) xylene and 1-(dimethylphenyl)1,3-diphenylbutane, are those recovered at a distillation temperature of 353°–377° C. and have a boiling point of 192°–230° C. at 3 mm Hg, a refractive index (n$_D^{20}$) of 1.5698–1.5700, a specific gravity (15°/4° C.) of 1.004–1.006, a bromine number of not more than 0.05, a pour point of −9° to −10° C., a kinetic viscosity (38° C.) of 560–570 cSt and a flash point of 208°–211° C. As is apparent from the foregoing, the alkylation product in the other aspect of this invention contains as the main component or components bis-(α-methylbenzyl) toluene and/or bis-(α-methylbenzyl) xylene and it has a boiling point of 340°–380° C. Thus, at least one of these compounds as the main components may substantially be obtained by fractionating the alkylation reaction product to obtain a fraction boiling in the range of 340°–380° C. The alkylation product may contain less than 10% by weight of other alkylates probably produced by introducing styrene into the unsubstituted aromatic ring of 2,2-diphenylethane derivatives (alkylation products of toluene and/or xylene with styrene), these being represented by the following formula

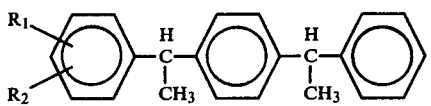

wherein R$_1$ is H or CH$_3$, R$_2$ is CH$_3$ or C$_2$H$_5$, but R$_2$ does not take C$_2$H$_5$ when R$_1$ takes CH$_3$; however, these compounds are not such that the effects or advantages of this invention are spoiled.

The hydrogenation in the other aspect of this invention is substantially the same as previously mentioned. In the hydrogenation step, ther may be used a diluent (reactive solvent) such as cyclohexane, n-hexane, methylcyclohexane, n-pentane or acetic acid. It is preferable that the hydrogenated alkylation reaction product be freed from the toluene, xylene, α-methylbenzyltoluene (α-phenyl-α-(methylphenyl) ethane) and/or α-methylbenzylxylene (α-phenyl-α-(dimethylphenyl) ethane) as decomposition products as well as from the tar and the like as polymerized material thereby to obtain a fraction boiling in the range of 330°–360° C. for use as a high viscosity traction fluid (traction fluid (II) of this invention).

The resulting hydrogenated bis-(α-methylbenzyl) toluene and (1-(methylphenyl)-1,3-diphenylbutane) contained in said fraction is bis-(α-cyclohexylethyl) methylcyclohexane and 1-(methylcyclohexyl)-1,3-dicyclohexylbutane having a boiling point of 331°–345° C. at atmospheric pressure or 207°–210° C. at 24 mm Hg, a specific gravity (15°/4° C.) of 0.88–0.89, a refractive index (n$_D^{20}$) of 1.486–1.487, a pour point of −19° to −21° C., a kinetic viscosity of 9.6–9.8 cSt (98.9° C.) or 146–148 cSt (37.8° C.) and a flash point of 200° C. The resulting hydrogenated bis-(α-methylbenzyl) xylene and 1-(dimethylphenyl)-1,3-diphenylbutane contained in said fraction are bis-(α-cyclohexylethyl) dimethylcyclohexane and 1-(dimethylcyclohexyl)-1,3-dicyclohexylbutane having a boiling point of 336°–360° C. at atmospheric pressure or 240°–244° C. at 27 mm Hg, a specific gravity (15°/4° C.) of 0.89–0.90, a refractive index (n$_D^{20}$) of 1.489–1.491, a pour point of −15° C., a kinetic viscosity of 10.7–10.9 cSt (98.9° C.) or 181–183 cSt (37.8° C.) and a flash point of 205°–210° C.

These hydrogenated compounds of toluene and/or xylene origin (traction fluids (II) of this invention) may be tested for their traction coefficient as previously mentioned. They have a traction coefficient of 0.092–0.094 (25° C.) or 0.072–0.074 (80° C.). Relatively high viscosity hydrocarbons, in hydrogenated form, synthesized for comparison have their respective traction fluids as follows. Hydrogenated polyisobutylene, 0.056; dicyclohexylmethylcyclohexane, 0.065; hydrogenated acenaphthene, 0.067; hydrogenated fluorene, 0.072; hydrogenated phenanthrene, 0.068; hydrogenated anthracene, 0.060; 1,3-tricyclohexylpropane, 0.062; tricyclohexylmethane, 0.057; hydrogenated 9-methylfluorene, 0.066; hydrogenated 9-phenylfluorene, 0.064; and adamantanes, 0.038. As is seen from the foregoing, the hydrogenated alkylation reaction products (traction fluids (II) of this invention) have a remarkably excellent coefficient as compared with the various synthesized hydrocarbons. It has been found that they (traction fluids (II) of this invention) have a still higher traction coefficient than hydrogenated α-methylstyrene linear dimer (0.085) which has been well known as a hydrocarbon having a high traction coefficient and a low viscosity lubricating, and that they are comparable to the previously mentioned traction fluid (I) having a traction coefficient of 0.088–0.092 although the former have a higher viscosity than the latter.

The traction fluids (II) of this invention have a viscosity of 9.8–10.9 cSt (98.9° C.). As required, it is of course possible to incorporate them with relatively low viscosity traction fluids to obtain traction fluids having an adjusted or desired viscosity. The traction fluids (I) (2–2.2 cSt at 98.9° C.) are particularly preferable for use as the relatively low viscosity traction fluids. The traction fluid (II) of this invention may be incorporated with the traction fluid (I) in an amount of 20–80 wt.%, preferably 30–50 wt.%, based on the total weight of the fluids (I) and (II) thereby to obtain a traction fluid having a viscosity of 2–11 cSt (98.9° C.).

In the alkylation reaction, reaction conditions may be selected so as to produce a 1:2 alkylation reaction product (toluene and/or xylene:styrene=1:2) simultaneously with producing a 1:1 alkylation reaction product (toluene and/or xylene:styrene=1:1) and, as required, the 1:1 alkylation reaction product once produced may be converted to a 1:2 alkylation reaction product by further alkylating the former with styrene, thereby to obtain a mixture of the 1:2 alkylation reaction product and the 1:1 alkylation reaction product. The mixture so obtained may be hydrogenated to obtain a traction fluid having a viscosity of 2–11 cSt (98.9° C.).

This invention will be better understood by the following Examples and Comparative Examples.

EXAMPLE 1 (XYLENE ALKYLATION TYPE SYSTEM)

Two liters of mixed xylene (o-32.8%, m-37.6%, p-19.6% and ethylbenzene 10%) and 600 g of a 85% sulphuric acid were introduced into a 5-liter stainless steel-made reactor where the resulting mixture was ice-cooled from outside and incorporated under agitation with a mixture of 250 cc styrene and 500 cc mixed xylene over a period of time of 20 minutes, during which the reaction temperature was maintained at 10°±5° C. The resulting reaction mixture was agitated for one hour, allowed to stand still and freed from the lower layer (sulphuric acid layer) by separation to obtain the upper layer (oil layer) which was incorporated with one liter of a 3% aqueous solution of sodium hydroxide and then agitated for 25 minutes. The mixture so agitated was then again allowed to stand still and freed from the lower layer (alkali layer) by separation to obtain the upper layer (oil layer) which was incorporated with 1.5 l of water and then agitated for 15 minutes. Such water washing was additionally effected four times. The oil layer so water washed was fed into a distillation tower having theoretical 10 stages where it was distilled at a bottoms temperature increasing to 315°–330° C. to distill off the unreacted xylene and ethylbenzene as the advance distillate and thereafter recover 400 cc of the alkylation reaction product (distillation temperature: 300°–319° C.). The distillate so recovered contained α-phenyl-α-(dimethylphenyl) ethane as the main component and the yield thereof is about 87% based on the styrene. This distillate had a specific gravity (15°/4° C.) of 0.987, a pour point of not higher than −48° C. and a bromine number of 0.1 and was not appreciated to contain linear dimer of styrene and cyclized dimer thereof.

The aforesaid alkylation reaction product (400 cc) was charged into a one-liter autoclave and incorporated with 35 g of Raney nickel, and thereafter hydrogen was forced into the autoclave until a hydrogen pressure of 35 Kg/cm$^2$ was reached. While agitating the alkylation reaction product in the autoclave, it was maintained at 60° C. for two hours, raised in temperature to 180° C. in 3 hours and then further heated to 180°–200° C. for 4 hours. The alkylation reaction product so treated was cooled to room temperature while still maintaining the reaction pressure at 35–40 Kg/cm$^2$, and the hydrogen was discharged from the autoclave. The contents from the autoclave were filtered to remove the catalyst therefrom and simultaneously obtain a filtrate. It was found from the NMR spectra of the thus obtained filtrate that at least 99.95 of the alkylation reaction product had been hydrogenated. The filtrate was distilled to remove a minute amount (1.8 g) of the decomposition products (xylene and ethylbenzene) and obtain 440 cc of a distillate boiling in the range of 288°–298° C. as a traction fluid (I). The distillate so obtained had a specific gravity (15°/4° C.) of 0.89, a refractive index ($n_D^{20}$) of 1.484, a pour point of −50° C., a viscosity of 0.5 poise (0° C.), a kinetic viscosity of 2.2 cSt (98.9° C.), a flash point of 140° C., a viscosity index of 5, and a traction coefficient of 0.092 (25° C.) or 0.071 (80° C.). One hundred and twenty (120) cc of the distillate or traction fluid (I) were incorporated with 1% of di-t.-butyl-p-cresol and oxidized under heat at an air flow of 5l/hr and at 350° F. for 72 hours in accordance with Federal 5308 with the results that the total acid value increased from the original 0.01 to only 0.21, the viscosity (100° F.) increased by 4%, the weight of the iron, copper, aluminum or magnesium used as the oxidizing catalyst varied very slightly by +0.01, −0.03, −0.01 or 0.00 mg/cm$^2$, and coke and sludges were not appreciated to be produced. From the above results it was found that the traction fluid had excellent stability even when placed under severely oxidizing conditions. It was further found that said traction fluid could very preferably be used in a Kopp variator because of its high traction coefficient and that the fatigue of rolling members caused by their rolling in the traction fluid was very slight.

EXAMPLE 2 (TOLUENE ALKYLATION SYSTEM)

Two thousand and five hundred (2,500) cc of toluene and 500 g of a 82% sulphuric acid were introduced into a 5-liter stainless steel-made reactor to form a mixture which was incorporated under agitation with 250 cc of styrene over a time period of 30 minutes while cooling the whole from outside. While maintaining the whole at a reaction temperature of 15°±5° C., it was agitated for additional 40 minutes after the end of addition of the styrene and then allowed to stand still for 30 minutes. The reaction mixture in the reactor was freed from the lower layer (sulphuric acid) by separation to obtain the upper layer (oil layer) which was incorporated with one liter of a 3% aqueous solution of sodium hydroxide and then agitated for 30 minutes. Thereafter, the lower layer (aqueous alkali solution layer) formed by allowing the alkali-added reaction mixture to stand still, was separated to obtain the upper layer (oil layer) which was incorporated with 1.5 liter of water and agitated for 10 minutes. After such water washing was additionally effected four times, the oil layer was fed into a distillation tower having theoretical 10 stages where it was distilled at a bottoms temperature increasing to 300°–315° C. to separate therefrom the unreacted toluene as the advance distillate and recover 353 cc of an alkylation reaction product (distillation temperature: (288°–298° C.). The distillate so recovered contained α-phenyl-α-tolylethane as the main component and the yield thereof was 82%, based on the styrene. This distillate had a specific gravity (15°/4° C.) of 0.985, a refractive index ($n_D^{17}$) of 1.566 and a bromine number of 0.1 and was not appreciated to contain linear dimer of styrene and cyclized dimer thereof.

350 cc of the aforesaid alkylation reaction product or distillate were charged into a one-liter autoclave and incorporated with 22 g of Raney nickel, and thereafter hydrogen was forced into the autoclave until a hydrogen pressure of 33 Kg/cm$^2$ was reached therein. The resulting mixture in the autoclave was maintained under agitation at 65° C. for two hours while replenishing the autoclave with hydrogen to maintain the reaction pressure therein at 30–40 Kg/cm$^2$, raised in temperature to 160° C. in 3 hours heated to 160°–180° C. for additional 4 hours, cooled to ambient temperature while maintaining the reaction pressure at 30–40 Kg/cm$^2$, freed from the hydrogen by discharging from the autoclave and then filtered to remove the catalyst and obtain a filtrate. It was found from the NMR (nuclear magnetic resonance) spectra of the thus obtained filtrate that at least 99.8% of the aforementioned alkylation reaction product had been hydrogenated. The filtrate was heated to distil off a minute amount (1.6 g) of the decomposition products (toluene and ethylbenzene) and obtain 405 cc of a distillate or traction fluid (I) boiling in the range of 269°–277° C. This distillate had a specific gravity (15°/4° C.) of 0.88, a refractive index ($n_D^{20}$) of 1.480, a pour point of not higher than −50° C., a viscosity of 0.5 poise (0° C.), a kinetic viscosity of 2 cSt (98.9° C.), a flash point of 137° C., a viscosity index of 6 and a traction coefficient of 0.090 (25° C.). This traction fluid was used in the same variable speed transmission in the same manner as in Example 1 with the result that it exhibited approximately the same excellent results as that of Example 1.

COMPARATIVE EXAMPLE 1 (STYRENE DIMERIZATION SYSTEM)

One thousand (1,000) cc of styrene containing 0.2% of t.-butylcatechol and an aqueous sulphuric acid solution prepared by mixing 100 cc of conc. H$_2$SO$_4$ and 150 cc of water, were mixed together under agitation and maintained at 120°–125° C. for 4 hours, cooled to 50° C. and allowed to stand still for one hour thereby to separate the oil layer which was incorporated with 250 cc of benzene for dilution and washed with an aqueous solution of sodium chloride and sodium carbonate. The oil layer so washed was then distilled to obtain a distillate containing linear styrene dimer (the distillate boiling in the range of 146°–153° C. at 3 mm Hg) in a yield of 76% (700 g). The distillate so obtained was charged into a distillation tower having theoretical 30 stages where it was again distilled to obtain 691 g of linear styrene dimer having a boiling point of 213.5° C. at 50 mm Hg, a refractive index ($n_D^{20}$) of 1.5927 or ($n_D^{23}$) of 1.5912 and a specific gravity (20°/4° C.) of 0.998 or (25°/4° C.) of 0.993. It was confirmed by gas chromatography that this distillate did not contain styrene trimer and contained cyclized styrene dimer in an amount of not more than only 0.5% (this fraction being hereinafter referred to as "linear styrene dimer A").

Styrene (880 g) containing 0.2 wt.% of t.-butylcatechol was added to one liter of 85.8 wt.% phosphoric acid and the resulting mixture was agitated, heated to 120° C. for 48 minutes, and cooled to 50° C. and allowed to stand still for 5 minutes, after which the oil layer was separated from the mixture. On the other hand, the acid layer was incorporated with 200 cc of benzene, extraction of the oil components present in the acid layer with the benzene was repeated five times and then the benzene solution obtained was combined with said oil layer. The benzene solution-added oil layer was water washed to remove the phosphoric acid therefrom, incorporated with 10 g. of t.-butylcatechol, freed from the benzene by distilling off at 70° C. and 3 mm Hg, and then distilled to obtain a distillate boiling in the range of 150°–200° C. at 20 mm Hg. This distillate was styrene dimer consisting of 61% linear dimer and 39% cyclic dimer. The remaining distillate was styrene trimer. Thus, the total distillate contained 18% of the trimer and 79% of the dimer totalling 97%, and the yield of tetramer was not more than 3% (the dimer, linear 61% and cyclic 39%, obtained herein being hereinafter referred to as "styrene dimer B").

Styrene (880 g) containing 0.2% of t.-butylcatechol was incorporated with one liter of 47% sulphuric acid, and the resulting mixture was agitated at 120° C. for two hours and cooled to 50° C. and allowed to stand still for 5 minutes, after which the oil layer was separated. The sulphuric acid layer was incorporated with 300 cc of benzene, and extraction with the benzene was repeated five times to obtain a benzene solution which was combined with the aforementioned oil layer. The combined mass was washed with water, incorporated with 10 g of t.-butylcatechol and distilled to obtain a distillate boiling in the range of 150°–200° C. at 20 mm Hg. Said distillate containing 91% linear styrene dimer and 9% cyclic styrene dimer was obtained in a yield of 81% (the distillate hereinafter referred to as "styrene dimer C"), while the remaining distillate consisting of styrene trimer was obtained in a yield of 15%.

Five hundred (500) grams of each of the styrene dimers A, B and C were charged into a one-liter autoclave, hydrogenated at a reaction pressure of 100 Kg/cm² and a reaction temperature of 215° C. for 8 hours in the presence of 50 g of a nickel-diatomaceous earth catalyst and filtered to separate the catalyst and obtain a filtrate. The filtrates so obtained were distilled to obtain distillates boiling in the range of 145°–148° C. at 8.5 mm Hg which were found from their infra-red spectra not to contain aromatic nuclei, respectively. They were measured for their traction coefficients with the result that the hydrogenated styrene dimers A, B and C had traction coefficients of 0.063, 0.059 and 0.061, respectively. These traction coefficients have been found to be remarkably unsatisfactory as compared with those of the hydrogenated alkylation reaction products (0.092~0.090) of xylene origin (Example 1) and toluene origin (Example 2) according to this invention.

COMPARATIVE EXAMPLE 2
(TOLUENE-CYCLOHEXENE ALKYLATION SYSTEM)

Nine hundred and twenty grams of toluene were incorporated with 10 g of aluminum chloride, and 6 l of hydrogen chloride gas were blown against the resulting mixture. The whole mass was incorporated with 1,640 g of cyclohexene and agitated for 4 hours. The thus agitated whole mass was washed with water 8 times, heated to distill off 250 g of the unreacted toluene and cyclohexene in total and then subjected to reduced pressure distillation thereby obtaining a distillate boiling in the range of 208°–214° C. at 20 mm Hg. The thus obtained distillate (boiling in the range of 340°–355° C. at atmospheric pressure) was found to be dicyclohexyltoluene from its molecular weight and infra-red absorption spectrum. This distillate, the yield of which was 90% (2340 g) based on the cyclohexene, had a pour point of not higher than −10° C., a flash point of 192° C., a refractive index ($n_D^{20}$) of 1.5360, a specific gravity (20°/4° C.) of 0.959, and a viscosity of 96.3 cSt (37.8° C.) or 5.56 cSt (98.9° C.). Five hundred (500) grams of the distillate were charged into an autoclave, hydrogenated at a reaction pressure of 100 Kg/cm² and reaction temperature of 215° C. for 10 hours in the presence of 50 g of a nickel-diatomaceous earth catalyst, and thereafter filtered to separate the catalyst and obtain a filtrate which was distilled to obtain a distillate boiling in the range of 160°–164° C. at 4 mm Hg. This distillate did not contain aromatic compounds and was found from its NMR spectra and gas chromatography to be dicyclohexylmethylcyclohexane boiling in the range of 320°–330° C. at atmospheric pressure, 140° C. at 20 mm Hg or 163° C. at 40 mm Hg. The distillate had a traction coefficient of 0.069 which was very unsatisfactory as compared with that (0.090) of the final product of toluene and styrene origin obtained in Example 2. In other words, styrene is suitable but cyclohexene is unsuitable as an alkylating agent for toluene.

COMPARATIVE EXAMPLE 3
(DIPHENYLMETHANE HYDROGENATION SYSTEM)

Two thousand one hundred and eighty (2,180) grams (2,060 cc) of benzyl alcohol and 1,560 g (1,780 cc) of benzene were introduced into a 10-liter flask, and 940 g of boron trifluoride gas was blown into the flask. The whole mass was transferred into an autoclave, agitated at 60° C. for 9 hours, heated, thereafter cooled and then separated into the lower layer (acid layer) and upper layer (oil layer). The upper layer (oil layer) was incorporated with 1.5 l of a 10% aqueous solution of sodium hydroxide, repeatedly agitated and washed eight times and then distilled to obtain 480 g of a distillate boiling in the range of 173°–176° C. at 72 mm Hg. This distillate had a boiling point of 261° C. at atmospheric pressure, 175° C. at 72 mm Hg, 149° C. at 29 mm Hg or 85° C. at 1 mm Hg, a specific gravity (30/4° C.) of 0.997, a viscosity of 0.01564 g/cm.sec (59° C.) ad a refractive index ($n_D^{25}$) of 1.570, and it was found to be diphenylmethane as the main ingredient from its NMR spectra and gas chromatography. The yield of the diphenylmethane was about 15% (about 460 g), and other distillates having a high boiling point such as dibenzylbenzene and tribenzylbenzene were produced in an amount of 989 g as by-products.

Four hundred and sixty (460) grams of diphenylmethane so obtained, 1.5 of ethanol and 60 g of a reduced nickel catalyst were introduced into an autoclave to form a mixture which was hydrogenated at 150° C. and 175 Kg/cm$^2$ for 7 hours and then distilled to obtain 440 g of a distillate boiling in the range of 249°–253° C. The distillate so obtained had a boiling point of 150° C. at 45 mm Hg, 131° C. at 19 mm Hg or 87° C. at 0.4 mm Hg, a secific gravity (20/4° C.) of 0.876 or (80/4° C.) of 0.834 and a refractive index ($n_D^{20}$) of 1.4755 or ($n_D^{80}$) of 1.4505, and the distillate was found to be dicyclohexylmethane. The distillate was measured for its traction coefficient and the result was 0.062. This traction coefficient (0.062) was unsatisfactory as compared with those (0.090–0.092) of the final products (traction fluids (I)) obtained in Examples 1 and 2.

COMPARATIVE EXAMPLE 4

Five hundred (500) grams of isobutylene hexamer and heptamer produced by the thermocracking of an isobutylene polymer obtained in the presence of aluminum chloride as the catalyst, and 50 g of a palladium-on-activated carbon catalyst were introduced into an autoclave to form a mixture which was subjected to hydrogenation at 275° C. and 100 Kg/cm$^2$ for 8 hours thereby to obtain a hydrogenated polyisobutylene having a viscosity index of 105 and a pour point of not higher than −51° C. This hydrogenated polyisobutylene had a traction coefficient of only 0.056.

COMPARATIVE EXAMPLE 5

Four hundred and eighty (480) grams of α-methylstyrene were incorporated with 97 g of titanium tetrachloride to form a mixture which was agitated at ambient temperature for 24 hours, diluted with 600 cc of benzene, washed three times with 200 cc of a 1 N-hydrochloric acid, washed three times with 200 cc of a 1 N-sodium hydroxide solution for neutralization and then washed 7 times with 300 cc of water. The oil layer of the mixture so treated was fractionated to obtain 304 g of a distillate boiling in the range of 115°–178° C. at 0.1 mm Hg. The thus obtained distillate was found to contain cyclic α-methylstyrene dimer and trimer as the main components from its NMR spectrum and gas chromatography. This distillate was further fractionated thereby to obtain 233 g of a fraction (cyclic dimer) boiling in the range of 115°–120° C. at 0.1 mm Hg. From the alkylation product so produced there were obtained, in addition to the aforesaid cyclic dimer and trimer, 48 g of a fraction (tetramer) boiling at 208°–212° C. at 0.1 mm Hg, 43 g of a fraction (pentamer) boiling at 240°–244° C. at 0.1 mm Hg, 41 g of a fraction (hexamer) boiling at 275°–285° C. at 0.1 mm Hg, 38 g (heptamer) boiling at 312°–316° C. at 0.1 mm Hg and 5 g of a fraction (octamer) boiling at 345°–360° C. at 0.1 mm Hg. Thus, the dimer fraction was obtained in a yield of only somewhat less than 50%. Two hundred and thirty (230) grams of the aforesaid dimer fraction having a boiling point of 118°–120° C. at 0.1 mm Hg, a specific gravity (20/4° C.) of 0.99 and a refractive index ($n_D^{20}$) of 1.563, together with 4 g of Raney nickel catalyst, were introduced into an autoclave to form a mixture. After hydrogen had been forced into the autoclave until a hydrogen pressure of 210 Kg/cm$^2$ was reached therein, the thus formed mixture was heated to 150°–220° C. while maintaining the hydrogen pressure at 210 Kg/cm$^2$ for 6 hours by replenishing the autoclave with hydrogen. The resulting reaction mixture was cooled to ambient temperature and filtered to obtain a filtrate which was distilled to remove therefrom 3 g of a distillate boiling in the range of not higher than 125° C. and recover a distillate boiling in the range of 110°–114° C. at 2 mm Hg. This distillate had a specific gravity (20/4° C.) of 0.890, a boiling point of 200° C. at 32 mm Hg, a refractive index ($n_D^{20}$) of 1.4875 and a viscosity of 0.208 g/cm.sec at 20° C., and it was considered to be a hydrogenated cyclic dimer of α-methylstyrene. This distillate had a traction coefficient (0.080) which was found to be considerably lower than (or inferior to) those (0.090–0.092) of the traction fluids (I) of this invention (Examples 1 and 2).

COMPARATIVE EXAMPLE 6

Thirty-five (35) grams of acid clay, 35 g of ethylene glycol and 610 g of α-methylstyrene were charged into a flask. The resulting mixture was agitated under reflux at 150° C. for one hour and then filtered to obtain a filtrate which was analyzed and found to contain the unreacted α-methylstyrene, 60 g of ethylene glcyol, about 520 g of linear α-methylstyrene dimer and about 50 g of other high molecular weight polymers. Said filtrate was heated to distil off the α-methylstyrene and ethylene glycol and then obtain 520 g of a distillate having a boiling point of 117°–120° C. at 0.1 mm Hg, a specific gravity (20/4° C.) of 0.989 and a refractive index ($n_D^{20}$) of 1.5675. The filtrate was found from gas chromatography to contain 94% of linear α-methylstyrene dimer and 6% of cyclic α-methylstyrene dimer. The residue (50 g) was α-methylstyrene trimer and tetramer. 500 g of said distillate boiling in the range of 171°–175° C. at 10 mm Hg and 48 g of Raney nickel catalyst were charged into an autoclave to form a mixture. After hydrogen had been forced into the autoclave until the hydrogen pressure therein reached 35 Kg/cm$^2$, the thus formed mixture was hydrogenated at 60° C. for two hours, at 180° C. for 3 hours and at 200° C. for one hour, thereafter cooled and filtered to remove the catalyst therefrom and obtain a filtrate. The thus obtained filtrate, which was found to contain less than 0.1% of the unsaturated materials, was distilled thereby to obtain a hydrogenated linear dimer distillate having a refractive index ($n_D^{20}$) of 1.4877, a specific gravity (20/4° C.) of 0.90, a boiling point of 194°–197° C. at 16 mm Hg, a kinetic viscosity of 3,500 cSt (−18° C.), 3.7 cSt (98.9° C.) or 22.7 cSt (37.8° C.), a viscosity index of 5, a flash point of 149° C. and a pour point of −44° C. This distillate had a traction coefficient (0.085) which was inferior to those (0.090–0.092) of the fluids (I) of this invention (Examples 1 and 2). It was also found that in the dimerization of α-methylstyrene in this Comparative Example, about 20% of by-products containing α-methylstyrene trimer and tetramer as the main components was obtained, while the yield (selective producibility) of the desired linear dimer was only about 80%.

EXAMPLE 3 (TOLUENE ALKYLATION SYSTEM)

A 250-ml pressure-proof cylindrical reactor, 4 cm dia. ×20 cm long, was filled with a synthetic silica alumina catalyst (aluminum content: 42 wt.%) previously subjected to baking treatment at 550° C. A mixture of toluene and styrene (molar ratio, 10:1; weight ratio, 9:1) heated to 147° C. was supplied at a flow rate of 247 cc/hr into the thus catalyst-filled reactor. The temperature and pressure within the reactor were maintained respectively at 144°–148° C. and 7.6–8 Kg/cm$^2$ thereby obtaining 23 Kg of the resulting effluent. The effluent so obtained was distilled to remove the unreacted toluene therefrom and recover 2.7 Kg of a distillate boiling in the range of 142°–144° C. at 11 mm Hg and 521 g of a fraction boiling in the range of 182°–200° C. at 3 mm Hg. The former was α-methylbenzyltoluene (α-phenyl-α-p-tolylethane, methylphenyl-p-tolylmethane) having a boiling point of 291°–293° C., a specific gravity (17/4° C.) of 0.987 and a refractive index ($n_D^{17}$) of 1.566, and the latter was 1-(methylphenyl)-1,3-diphenylbutane and bis-(α-methylbenzyl) toluene having a boiling point of 348°–362° C., a refractive index ($n_D^{20}$) of 1.5665 and a specific gravity (15/4° C.) of 0.985, these facts being found from the NMR spectra, infra-red absorption spectra, gas chromatographies and mass spectra of the aforesaid two distillates. Although 280 g of styrene polymers were obtained as the residue after the aforesaid distillation, 70% of the styrene was converted to α-methylbenzyltoluene, and 17% of the styrene was converted to bis-(α-methylbenzyl) toluene and 1-(methylphenyl)-1,3-diphenylbutane; thus, it was found that 87% of the styrene had been consumed for alkylation with the toluene. The bis-(α-methylbenzyl) toluene and 1-(methylphenyl)-1,3-diphenylbutane distillate had a bromine number of not more than only 0.05, and low polymers of styrene were not detected therein. Then, 340 g of this distillate were charged into a 2-liter autoclave, incorporated with 25 g of a nickel-on-diatomaceous earth catalyst (nickel content: 65%) and further incorporated with 300 cc of n-hexane as the diluting solvent to form a mixture. After hydrogen had been forced into the autoclave until the hydrogen pressure therein reached 105 Kg/cm$^2$, the mixture so formed was heated under agitation to 65° C. for two hours and then to 135° for 4 hours while replenishing the autoclave with hydrogen to maintain the hydrogen pressure at 100–105 Kg/cm$^2$. Thereafter, the mixture so heated was cooled to ambient temperature to discharge the hydrogen from the autoclave and then filtered to remove the catalyst and obtain a filtrate. It was found from the NMR spectra of the filtrate that at least 99.8% of the toluene alkylation product had been hydrogenated. The thus obtained filtrate was distilled to recover the n-hexane, remove a very small amount (1.1 g) of the decomposition products (toluene, ethylbenzene) and then obtain 370 cc of a distillate boiling in the range of 207°–210° C. at 24 mm Hg as a traction fluid (II) of this invention. This distillate or traction fluid (II) was bis-(α-cyclohexylethyl) methylcyclohexane and 1-(methylcyclohexyl)-1,3-dicyclohexylbutane having a specific gravity (15/4° C.) of 0.89, a refractive index ($n_D^{20}$) of 1.487, a boiling point of 331°–345° C., a kinetic viscosity of 9.8 cSt (98.9° C.), a flash point of 200° C. and a traction coefficient of 0.094.

Said traction fluid (120 cc) was incorporated with 1% of di-t.-butyl-p-cresol as the oxidation inhibitor and then thermally oxidized at 350° F. and an air flow rate of 5 l/hr for 72 hours in accordance with Federal 5308. The result was that the total oxidation increased from the original 0.01 to only 0.21, the viscosity (100° F.) increased by 4%, metal samples (such as iron, copper, aluminum and magnesium) used as the oxidation catalyst varied in weight respectively by only +0.01, −0.03, −0.01 and 0.00 mg/cm$^2$, and production of coke and sludges was not appreciated, this indicating that said traction fluid exhibited excellent stability (quality) even under such severe oxidizing conditions. It was further found that when the traction fluid was used in a Kopp variator, it exhibited very satisfactory performance because of its high traction coefficient, and that the fatigue of the rolling members caused by rolling was very slight.

EXAMPLE 4 (XYLENE ALKYLATION SYSTEM)

A 17-Kl reactor was charged with 1 Kl/hr of xylene (mixed xylene for industrial use: o-xylene, 33%; m-xylene, 37%; p-xylene, 20%; and ethylbenzene, 10%), 0.3 Kl/hr of styrene, 31.5 Kl/hr of circulating xylene and 0.5 Kl/hr of sulphuric acid (92%) to form a mixture (average residence time: about 30 minutes) which was so cooled from outside as to maintain the reaction temperature at 10° C. The resulting effluent was allowed to stand still to separate the lower layer (sulphuric acid layer) for re-circulation and obtain the upper layer (oil layer). The upper layer so obtained was neutralized with an aqueous solution of sodium hydroxide, washed with water and distilled to recover the unreacted xylene for re-use as circulating xylene and then obtain 430 Kg/hr of a distillate boiling in the range of 300°–319° C. at atmospheric pressure and 56 Kg/hr of a distillate boiling in the range of 193°–220° C. at 3 mm Hg. The former was a mixture (specific gravity (15/4° C.): 0.987) of α-methylbenzylxylene and α-methylbenzylethylbenzene (9:1) and the latter was a mixture of bis-(α-methylbenzyl) xylene and bis-(α-methylbenzyl) ethylbenzene (9:1), the mixture having a refractive index ($n_D^{20}$) of 1.5701, a specific gravity (15/4° C.) of 1.006, a kinetic viscosity of 570 cSt at 37.8° C. and a flash point of 211° C. As the residue after the distillation, 37 Kg/hr of styrene polymers were obtained. Eighty (80)% of the styrene and 7.5% thereof were converted respectively to the α-methylbenzylxylene/α-methylbenzylethylbenzene mixture and the bis-(α-methylbenzyl) xylene/bis-(α-methylbenzyl) ethylbenzene mixture and, thus, it was found that a total of 87.5% of the styrene was consumed in the alkylation. The bis-(α-methylbenzyl) xylene/bis-(α-methylbenzyl) ethylbenzene mixed distillate had a bromine number of not more than only 0.05, and low polymers of styrene were not detected. Four hundred (400) grams of this mixed distillate were charged into a 2-liter autoclave and incorporated with 13 g of a rhodium-activated carbon catalyst and 550 cc of methylcyclohexane as the solvent for dilution, after which hydrogen was forced into the autoclave until a hydrogen pressure of 200 Kg/cm$^2$ therein was reached. The whole mass in the autoclave was heated to 50° C. for one hour, at 100° C. for 30 minutes and at 150° C. for 3 hours. The whole mass so heated was cooled to ambient temperature and, after discharge of the hydrogen, filtered to remove the catalyst and obtained a filtrate. From the analysis of the thus obtained filtrate it was found that at least 99.8% of the xylene alkylation reaction product had been hydrogenated. The filtrate was distilled to recover the methylcyclohexane, remove a minute amount of decomposition products (xylene and ethylbenzene) and then obtain 440 cc of a distillate (traction fluid (II)) boiling in the range of 241°–244° C. at 27 mm Hg. The distillate so obtained was a mixture of bis-(α-cyclohexylethyl) dimethylcyclohexane and bis-(α-cyclohexylethyl) ethylcyclohexane, the mixture having a specific gravity (15/4° C.) of 0.90, a refractive index ($n_D^{20}$) of 1.491 and a kinetic viscosity of 10.9 cSt (98.9° C.), a flash point of 205° C. and a traction coefficient of 0.092 at ambient temperature or 0.074 at 80° C. In addition, when this traction fluid was used in the same traction drive transmission in the same manner as in Example 3, it exhibited the same excellent result as that obtained in Example 3.

EXAMPLE 5 (α-METHYLBENZYLXYLENE ALKYLATION SYSTEM)

Twenty-one (21) Kl/hr of the distillate (a mixture of α-methylbenzylxylene and α-methylbenzylethylbenzene) boiling in the range of 300°–319° C. obtained in Example 2, 0.1 Kl/hr of styrene and 0.4 Kl/hr of sulphuric acid (92%) were supplied into a 17-Kl reactor (average residence time: about 48 minutes) and so cooled from outside as to maintain the reaction temperature at 14° C. The resulting effluent from the autoclave was allowed to stand still thereby to separate the lower layer (sulphuric acid) for re-circulation and obtain the upper layer (oil layer). The upper layer so obtained was neutralized with an aqueous solution of sodium hydroxide, washed with water and distilled to recover the unreacted α-methylbenzylxylene/α-methylbenzylethylbenzene mixture for re-circulation and then obtain 270 Kg/hr of a distillate boiling in the range of 193°–220° C. at 3 mm Hg. This distillate was found to be a mixture corresponding to the bis-(α-methylbenzyl) xylene/bis-(α-methylbenzyl) ethylbenzene mixture (9:1) obtained in Example 4. As the residue (after the distillation), 3 Kg/hr of styrene polymers was obtained. Thus, it was found that 95% of the styrene was consumed for the alkylation. Four hundred (400) grams of the aforesaid distillate boiling in the range of 193°–220° C. at 3 mm Hg were hydrogenated to obtain 440 cc of a bis-(α-cyclohexylethyl) dimethylcyclohexane/bis-(α-cyclohexylethyl) ethylcyclohexane mixture (traction fluid (II) of this invention) having a specific gravity (15/4° C.) of 0.90, a refractive index ($n_D^{20}$) of 1.490, a kinetic viscosity of 10.9 cSt (98.9° C.), and a traction coefficient of 0.093 (25° C.) or 0.075 (80° C.).

When this mixture was used as the traction fluid in the same traction drive transmission in the same manner as in Example 3, it exhibited approximately the same excellent performance as that obtained in Example 3.

EXAMPLE 6

(1) Polymerization of styrene

One gram of $CF_3SO_3H$ as catalyst was dissolved in 1 l of cyclohexane as a solvent. The resulting solution was maintained at 60° C. under agitation, incorporated with 750 g of styrene while cooling the whole to inhibit the temperature rise thereof due to the heat of reaction, and then maintained at 50° C. under agitation for 120 minutes thereby completing the reaction. Then, the resulting reaction mixture was neutralized and washed with water to remove the catalyst therefrom. The reaction mixture so treated was heated to distil off the cyclohexane at a reduced pressure of 100 mm Hg and then distilled at a reduced pressure of 3 mm Hg thereby to obtain 575 g of a dimer distillate (distillation-off temperature: 140°–155° C.) and 155 g of the residue.

The dimer distillate so obtained was a mixture of 97% of 1,3-diphenylbutene-1 which was an unsaturated dimer and 3% of 1-methyl-3-phenylindane which was a saturated dimer. Said residue was then subjected to a high vacuum distillation at 0.1 mm Hg thereby to obtain 140 g of a distillate at a distillation temperature 150°–220° C. This distillate was found to be a mixture of styrene trimer and tetramer by liquid chromatography.

(2) Alkylation

Ten (10) grams of $CF_3SO_3H$ as alkylating catalyst were dissolved in 2000 g of xylene, heated to 60° C. and incorporated with 500 g of the styrene dimer distillate, obtained in said Styrene Polymerization (1), over a period of time of one hour. The resulting mixture was then reacted at 60° C. for additional two hours. After the end of the reaction, the reaction mixture was neutralized and washed with water to remove the catalyst therefrom.

The reaction mixture so treated was heated to recover the unreacted xylene at atmospheric pressure, distilled at a reduced pressure of 3 mm Hg to recover 30 g of a distillate at a distillation temperature of 130°–155° C. and then 630 g of a distillate at a distillation temperature of 190°–230° C. The lighter distillate was 1-methyl-3-phenylindane which was saturated dimer of styrene, while the heavier distillate was found to be 1-(dimethylphenyl)-1,3-diphenylbutane which was an alkylation product of xylene and unsaturated dimer of styrene.

(3) Hydrogenation

Two hundred and twenty (220) grams of the heavier distillate (1-dimethylphenyl-1,3-diphenylbutane) obtained in said Alkylation (2) as well as 18 g of Raney nickel were charged into a 1-liter autoclave which was then connected through a pressure-regulating valve to a hydrogen Bombe to maintain the inside thereof at a hydrogen pressure of 35 atm. The contents of the Bombe were, under agitation, heated to 100° C. for 3 hours, to 160° C. for 4 hours and then to 180° C. for 3 hours for hydrogenation. The resulting mixture was cooled and filtered to remove the Raney nickel and obtain 230 g of a hydrogenated heavy fraction. The thus obtained heavy fraction was again distilled at a reduced pressure of 3 mm Hg to remove the decomposed materials produced in the hydrogenation step and obtain 278 g of a distillate at a distillation temperature of 190°–230° C. This distillate was a traction fluid (fluid (II)) of this invention. The traction fluid (II) was a colorless liquid having a specific gravity of 0.894 (15/4° C.), a viscosity of 181 cSt at 100° F. (38° C.) or 10.7 cSt at 210° F. (99° C.) and a flash point of 210° C. In addition, it was found by ultraviolet light absorption analysis that the residual phenyl groups present were 0.37 mol %, this indicating that said traction fluid was substantially 1-(dimethylcycloxyl)-1,3-dicyclohexylbutane.

COMPARATIVE EXAMPLE 7

Four liters of an ethyl ether solution containing 500 g of benzyl magnesium chloride were added slowly to a mixture of 1.5 Kg benzoyl chloride and 1 l of ethyl ether while cooling the whole mass. Thereafter, the whole mass was incorporated with 1 l of 30% sulphuric acid, agitated, incorporated with an alkali for neutralizing the sulphuric acid, washed with water and then distilled to remove therefrom 183 g of a distillate (phenyl-o-tolylketone) boiling in the range of 164°–169° C. at 9 mm Hg and then obtain 200 g of a distillate (1,2,3-triphenylpropanol) boiling in the range of 224°–235° C. at 8 mm Hg. This propanol (180 g) was incorporated with 150 cc of toluene and 35 g of potassium sulphite to form a mixture which was heated under reflux and, after distillation-off of the toluene, obtain 153 g of 1,2,3-triphenylpropene-1 as the distillate boiling in the range of 185°–188° C. at 0.03 mm Hg. The thus obtained distillate (128 g) was incorporated with 14 g of a rhodium-activated carbon catalyst (rhodium content: 5 wt.%) and 500 cc of n-hexane in a 2-liter autoclave where the resulting mixture was heated to 65° C. for 20 minutes and then at 95° C. for one hour under a hydrogen pressure of 100 Kg/cm$^2$, and further heated to 200° C. for 5 hours under a hydrogen pressure of 200 Kg/cm$^2$ to distil off the n-hexane and then obtain 124 g of a distillate boiling in the range of 140°-146° C. at 0.025 mm Hg and having a refractive index ($n_D{}^{25}$) of 1.4959. It was found from the NMR spectrum of this distillate that at least 95% of hydrogenation of the aromatic nuclei and aliphatic unsaturated bonds in the distillate had been effected. The distillate was 1,2,3-tricyclohexylpropane having a kinetic viscosity of 7.69 cSt (98.9° C.) and a traction coefficient of 0.075. The distillate or conventional traction fluid obtained herein had a comparatively high viscosity but it was very unsatisfactory in traction coefficient as compared with the traction fluids (II) of this invention (traction coefficient: 0.092~0.094 as indicated in Examples 3–5). Further, it is very uneconomical that the synthesis of such a conventional traction fluid will require a Grignard's reaction using benzyl magnesium chloride and benzoyl chloride.

As is seen from the foregoing, according to this invention, there may be obtained lubricating oils or traction fluids having a high traction coefficient and, for some purposes, a high viscosity such as 9.8–10.9 cSt (98.9° C.) from easily available inexpensive toluene (or xylene) and styrene by the use of simple synthesizing methods.

What is claimed is:

1. In a traction drive transmission having a traction fluid, the improvement in which said traction fluid comprises at least one compound selected from the group consisting of α-cyclohexyl-α-methyl-cyclohexylethane and α-cyclohexyl-α-dimethylcyclohexylethane and mixtures thereof, the at least one compound being obtained by hydrogenating at least one compound selected from the group consisting of α-phenyl-α-tolylethane and α-phenyl-α-(dimethylphenyl) ethane as alkaylation products of (A) at least one member selected from the group consisting of xylene and toluene and mixtures thereof, and (B) styrene.

2. In a traction drive transmission having a traction fluid, the improvement in which said traction fluid comprises a mixture of (1) at least one compound selected from the group consisting of α-cyclohexyl-α-methylcyclohexylethane and α-cyclohexyl-α-dimethylcyclohexylethane and mixtures thereof with (2) α-cyclohexyl-α-ethylcyclohexyl-ethane, the mixture being obtained by hydrogenating a mixture of (1) at least one compound selected from the group consisting of α-phenyl-α-methylphenylethane and α-phenyl-α-(dimethylphenyl) ethane and mixtures thereof with (2) α-phenyl-α-ethylphenylethane, the compounds (1) and (2) to be hydrogenated being alkylation products of (A) a mixture of (1) at least one member selected from the group consisting of xylene and toluene and mixtures thereof with (2) less than 50%, based on the xylene and/or toluene used, by weight of ethylbenzene and (B) styrene.

3. In a traction drive transmission having a traction fluid, the improvement in which said traction fluid comprises at least one compound selected from the group consisting of bis-(α-cyclohexylethyl) methylcyclohexane and bis-(α-cyclohexylethyl)-dimethylcyclohexane and mixtures thereof, the at least one compound being obtained by hydrogenating at least one compound selected from the group of bis-(α-methylbenzyl) toluene and bis-(α-methylbenzyl) xylene and mixtures thereof as alkylation products of (A) xylene and/or toluene with (B) styrene.

4. In a traction drive transmission having a traction fluid, the improvement in which said traction fluid comprises a mixture of (1) at least one compound selected from the group consisting of bis-(α-cyclohexylethyl)-methyl-cyclohexane and bis-(α-cyclohexylethyl)dimethylcyclohexane and mixtures thereof with (2) bis-(α-cyclohexylethyl) ethylcyclohexane, the mixture being obtained by hydrogenating a mixture of (1) at least one compound selected from the group consisting of bis-(α-methylbenzyl) toluene and bis-(α-methylbenzyl) xylene and mixtures thereof with (2) bis-(α-methylbenzyl)ethylbenene, the compounds (1) and (2) to be hydrogenated being alkylation products of (A) a mixture of (1) xylene and/or toluene with (2) less than 50%, based on the xylene and/or toluene used, by weight of ethylbenzene and (B) styrene.

5. In a traction drive transmission having a traction fluid, the improvement in which said traction fluid comprises at least one compound selected from the group consisting of 1-(methylcyclohexyl)-1,3-dicyclohexylbutane and 1-(dimethylcyclohexyl)-1,3-dicyclohexylbutane and mixtures thereof, obtained by hydrogenating at least one compound selected from the group consisting of 1-(methylphenyl)-1,3-diphenylbutane and 1-(dimethylphenyl)-1,3-diphenylbutane and mixtures thereof as alkylation products of (A) xylene and/or toluene and (B) styrene.

6. In a traction drive transmission having a traction fluid, the improvement in which said traction fluid comprises a mixture of (1) at least one compound selected from the group consisting of 1-(methylcyclohexyl)-1,3-dicyclohexylbutane and 1-(dimethylcyclohexyl)-1,3-cyclohexylbutane and mixtures thereof with (2) 1-(ethylcyclohexyl)-1,3-dicyclohexylbutane, the mixture being obtained by hydrogenating a mixture of (1) at least one compound selected from the group consisting of 1-(methylphenyl)-1,3-diphenylbutane and 1-(dimethylphenyl)-1,3-diphenylbutane and mixtures thereof with (2) 1-(ethylphenyl)-1,3-diphenylbutane, the compounds (1) and (2) to be hydrogenated being alkylation products of (A) a mixture of (2) xylene and/or toluene with (2) less than 50%, based on the xylene and/or toluene used, by weight of ethylbenzene and (B) styrene.

7. In a traction drive transmission having a traction fluid composition, the improvement in which said traction fluid composition comprises a compound of the following structural formula:

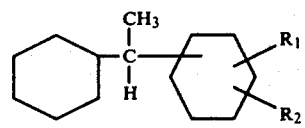

wherein $R_1$ is H or $CH_3$, $R_2$ is $CH_3$ or $C_2H_5$, provided that $R_2$ is $CH_3$ when $R_1$ is $CH_3$.

8. In a traction drive transmission having a traction fluid composition, the improvement in which said traction fluid composition comprises a compound of the following structural formula:

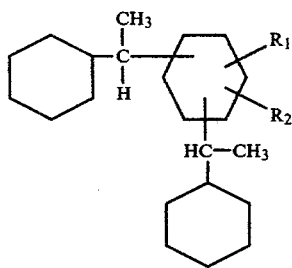

wherein $R_1$ is H or $CH_3$, $R_2$ is $CH_3$ or $C_2H_5$, provided that $R_2$ is $CH_3$ when $R_1$ is $CH_3$.

9. In a traction drive transmission having a traction fluid composition, the improvement in which said traction fluid composition comprises a compound of the following formula:

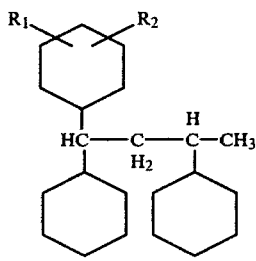

wherein $R_1$ is H or $CH_3$, $R_2$ is $CH_3$ or $C_2H_5$, provided that $R_2$ is $CH_3$ when $R_1$ is $CH_3$.

10. In a traction drive transmission according to claim 7 wherein the compound is α-cyclo-hexyl-α-methylcyclohexylethane.

11. In a traction drive transmission according to claim 7 wherein the compound is α-cyclohexyl-α-dimethylcyclohexylethane.

12. In a traction drive transmission according to claim 7 wherein the compound is α-cyclohexyl-α-ethylcyclohexylethane.

13. In a traction drive transmission according to claim 8 wherein the compound is bis-(α-cyclohexylethyl)methylchclohexane.

14. In a traction drive transmission according to claim 8 wherein the compound is bis-(αcyclohexylethyl)dimethylcyclohexane.

15. In a traction drive transmission according to claim 8 wherein the compound is bis-(α-cyclohexylethyl)ethylcyclohexane.

16. In a traction drive transmission according to claim 9 wherein the compound is 1-(methylcyclohexyl)-1,3-dicyclohexylbutane.

17. In a traction drive transmission according to claim 9 wherein the compound is 1-(dimethylcyclohexyl)-1,3-dicyclohexylbutane.

18. In a traction drive transmission according to claim 9 wherein the compound is 1-(ethylcyclohexyl)-1,3-dicyclohexylbutane.

19. In a traction drive transmission according to claims 8 or 9 having a kinetic viscosity of about 3–11 cSt.

20. A process of improving the rolling friction of fluids used in traction drive transmissions comprising the steps of:
  (A) alkylating at least one compound selected from the group consisting of xylene, toluene, and mixtures thereof with styrene,
  (B) hydrogenating the resulting alkylation product, and
  (C) using the resulting hydrogenated product in a traction drive transmission to thereby improve the rolling friction thereof.

21. The process according to claim 20 wherein ethylbenzene is additionally included in step (A) in an amount not more than 50% by weight of the compound selected from the group consisting of xylene, toluene, and mixtures thereof.

22. The process of claim 21 wherein sulfuric acid is used as the catalyst in step (A).

* * * * *